(12) United States Patent
Kim et al.

(10) Patent No.: US 9,297,030 B2
(45) Date of Patent: Mar. 29, 2016

(54) METHOD FOR THE PREPARATION OF NICOTINIC ACID

(75) Inventors: So Young Kim, Gyeonggi-do (KR); Yong Uk Shin, Gyeonggi-do (KR); In Kyung Heo, Seoul (KR); Ju Eun Kim, Seoul (KR); Sung Kwang Son, Seoul (KR); Chang Il Seo, Incheon (KR); Hyun Ah Kim, Jeollabuk-do (KR); Han Jin Lee, Seoul (KR); Kwang Ho Na, Seoul (KR); Jee Yeon Bae, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 15 days.

(21) Appl. No.: 13/979,673

(22) PCT Filed: Jan. 16, 2012

(86) PCT No.: PCT/KR2012/000370
§ 371 (c)(1),
(2), (4) Date: Sep. 24, 2013

(87) PCT Pub. No.: WO2012/096553
PCT Pub. Date: Jul. 19, 2012

(65) Prior Publication Data
US 2014/0315263 A1 Oct. 23, 2014

(30) Foreign Application Priority Data

Jan. 14, 2011 (KR) .................. 10-2011-0004093

(51) Int. Cl.
*C12P 17/12* (2006.01)
*C07D 213/80* (2006.01)

(52) U.S. Cl.
CPC .............. *C12P 17/12* (2013.01); *C07D 213/80* (2013.01)

(58) Field of Classification Search
None
See application file for complete search history.

(56) References Cited

U.S. PATENT DOCUMENTS

| 6,689,587 | B2 | 2/2004 | Bastuck et al. |
| 6,692,946 | B2 | 2/2004 | Bastuck et al. |
| 2002/0137163 | A1 | 9/2002 | Bastuck et al. |
| 2002/0137169 | A1 | 9/2002 | Bastuck et al. |

FOREIGN PATENT DOCUMENTS

| CN | 101353322 | 1/2009 |
| EP | 0279273 | 8/1988 |
| KR | 920008365 | 9/1992 |

OTHER PUBLICATIONS

Extended European Search Report for EP 12734376.2, Completed by the European Patent Office on Apr. 8, 2015, 7 pages.
Flachmann et al. Eur. J. Biochem. 1988, vol. 175, p. 221-228, "Molecular biology of pyridine nucleotide biosynthesis in *Escherichia coli*, Cloning and characterization of quinolinate synthesis genes andA and nadB.".
International Search Report for PCT/KR2012/000370, Completed by the Korean Patent Office on Sep. 4, 2012, 3 pages.
Gerasimova., Journal of Bioinformatics and Computational Biology 2005, vol. 3, No. 4, p. 1007-1019, "Evolution of the NADR Regulon in Enterobacteriaceae.".
Baba et al. Molecular Systems Biology 2006, 11 pages, "Construction of *Escherichia coli* K-12 in-frame, single-gene knockout mutants: the Keio collection.".
Chandler et al. Journal of Bacteriology 1972, vol. 111, No. 1, p. 98-102, "De Novo Biosynthesis of Nicotinamide Adenine Dinucleotide in *Escherichia coli* : Excretion of Quinolinic Acid by Mutants Lacking Quinolinate Phosphoribosyl Transferase.".
Chuck., Applied Catalysis A: General 2005, vol. 280, p. 75-82, "Technology development in nicotinate production.".
Fu et al. Ind.Eng. Chem. Res. 2009, vol. 48, p. 10467-10471, "Hydrothermal Decarboxylation of Pentafluorobenzoic Acid and Quinolinic Acid.".

*Primary Examiner* — Nashaat Nashed
(74) *Attorney, Agent, or Firm* — Brooks Kushman P.C.

(57) ABSTRACT

A method for the preparation of nicotinic acid, which includes the step of obtaining a culture solution containing quinolinic acid by incubating a microorganism having an ability to produce quinolinic acid, and the step of adding an acid to the culture solution and conducting a decarboxylation reaction.

13 Claims, 3 Drawing Sheets hydrothermal decarboxylation

SEQUENCE LISTING

```
<160> NUMBER OF SEQ ID NOS: 21

<210> SEQ ID NO 1
<211> LENGTH: 25
<212> TYPE: DNA
<213> ORGANISM: Artificial Sequence
<220> FEATURE:
<223> OTHER INFORMATION: primer for amplification of nadB

<400> SEQUENCE: 1
catatgaata ctctccctga acatt                                           25

<210> SEQ ID NO 2
<211> LENGTH: 28
<212> TYPE: DNA
<213> ORGANISM: Artificial Sequence
<220> FEATURE:
<223> OTHER INFORMATION: primer for amplification of nadB

<400> SEQUENCE: 2
ggatccctat accactacgc ttgatcac                                        28

<210> SEQ ID NO 3
<211> LENGTH: 27
<212> TYPE: DNA
<213> ORGANISM: Artificial Sequence
<220> FEATURE:
<223> OTHER INFORMATION: primer for amplification of nadA

<400> SEQUENCE: 3
gggcccatga gcgtaatgtt tgatcca                                         27

<210> SEQ ID NO 4
<211> LENGTH: 25
<212> TYPE: DNA
<213> ORGANISM: Artificial Sequence
<220> FEATURE:
<223> OTHER INFORMATION: primer for amplification of nadA

<400> SEQUENCE: 4
gcggccgctc gtgcctaccg cttcg                                           25

<210> SEQ ID NO 5
<211> LENGTH: 25
<212> TYPE: DNA
<213> ORGANISM: Artificial Sequence
<220> FEATURE:
<223> OTHER INFORMATION: primer for amplification of cysK promoter

<400> SEQUENCE: 5 ggatcccag cctgtttacg atgat                                            25

<210> SEQ ID NO 6
<211> LENGTH: 28
<212> TYPE: DNA
```

```
<213> ORGANISM: Artificial Sequence
<220> FEATURE:
<223> OTHER INFORMATION: primer for amplification of cysK promoter

<400> SEQUENCE: 6
gggccctcct taactgtatg aaattggg                                            28

<210> SEQ ID NO 7
<211> LENGTH: 20
<212> TYPE: DNA
<213> ORGANISM: Artificial Sequence
<220> FEATURE:
<223> OTHER INFORMATION: primer for amplification of downstream region
      of nadC

<400> SEQUENCE: 7
gaaacgggaa agcagattcc                                                     20

<210> SEQ ID NO 8
<211> LENGTH: 41
<212> TYPE: DNA
<213> ORGANISM: Artificial Sequence
<220> FEATURE:
<223> OTHER INFORMATION: primer for amplification of downstream region
      of nadC

<400> SEQUENCE: 8
cggtaggtac cgagctcgaa aagtagagaa tctggaagaa c                             41

<210> SEQ ID NO 9
<211> LENGTH: 41
<212> TYPE: DNA
<213> ORGANISM: Artificial Sequence
<220> FEATURE:
<223> OTHER INFORMATION: primer for amplificaiton of loxCm

<400> SEQUENCE: 9
gttcttccag attctctact tttcgagctc ggtacctacc g                             41

<210> SEQ ID NO 10
<211> LENGTH: 42
<212> TYPE: DNA
<213> ORGANISM: Artificial Sequence
<220> FEATURE:
<223> OTHER INFORMATION: primer for amplification of loxpCm

<400> SEQUENCE: 10
tgaagaggtg tttattcaac tggggggtacc gttcgtataa tg                           42

<210> SEQ ID NO 11
<211> LENGTH: 42
<212> TYPE: DNA
<213> ORGANISM: Artificial Sequence
<220> FEATURE:
<223> OTHER INFORMATION: primer for amplification of upstream region of
      nadC

<400> SEQUENCE: 11
cattatacga acggtacccc cagttgaata aacacctctt ca                            42

<210> SEQ ID NO 12
<211> LENGTH: 19
<212> TYPE: DNA
<213> ORGANISM: Artificial Sequence
<220> FEATURE:
<223> OTHER INFORMATION: primer for amplification of upstream region of
      nadC
```

<400> SEQUENCE: 12
gtggtgctaa tacccggtt                                                    19

<210> SEQ ID NO 13
<211> LENGTH: 1623
<212> TYPE: DNA
<213> ORGANISM: Escherichia coli
<220> FEATURE:
<221> NAME/KEY: gene
<222> LOCATION: (1)..(1623)
<223> OTHER INFORMATION: nadB ORF

<400> SEQUENCE: 13

| | |
|---|---|
| atgaatactc tccctgaaca ttcatgtgac gtgttgatta tcggtagcgg cgcagccgga | 60 |
| cttttcactgg cgctacgcct ggctgaccag catcaggtca tcgttctaag taaaggcccg | 120 |
| gtaacggaag gttcaacatt ttatgcccag ggcggtattg ccgccgtgtt tgatgaaact | 180 |
| gacagcattg actcgcatgt ggaagacaca ttgattgccg gggctggtat ttgcgatcgc | 240 |
| catgcagttg aatttgtcgc cagcaatgca cgatcctgtg tgcaatggct aatcgaccag | 300 |
| ggggtgttgt ttgataccca cattcaaccg aatggcgaag aaagttacca tctgacccgt | 360 |
| gaaggtggac atagtcaccg tcgtattctt catgccgccg acgccaccgg tagagaagta | 420 |
| gaaaccacgc tggtgagcaa ggcgctgaac catccgaata ttcgcgtgct ggagcgcagc | 480 |
| aacgcggttg atctgattgt ttctgacaaa attggcctgc cggcacgcg acgggttgtt | 540 |
| ggcgcgtggg tatggaaccg taataaagaa acggtggaaa cctgccacgc aaaagcggtg | 600 |
| gtgctggcaa ccggcggtgc gtcgaaggtt tatcagtaca ccaccaatcc ggatatttct | 660 |
| tctggcgatg gcattgctat ggcgtggcgc gcaggctgcc gggttgccaa tctcgaattt | 720 |
| aatcagttcc accctaccgc gctatatcac ccacaggcac gcaatttcct gttaacagaa | 780 |
| gcactgcgcg cgaaggcgc ttatctcaag cgcccggatg gtacgcgttt tatgcccgat | 840 |
| tttgatgagc gcggcgaact ggccccgcgc gatattgtcg cccgcgccat tgaccatgaa | 900 |
| atgaaacgcc tcggcgcaga ttgtatgttc cttgatatca gccataagcc cgccgatttt | 960 |
| attcgccagc atttcccgat gatttatgaa aagctgctcg gctgggat tgatctcaca | 1020 |
| caagaaccgg taccgattgt gcctgctgca cattatacct gcggtggtgt aatggttgat | 1080 |
| gatcatgggc gtacggacgt cgagggcttg tatgccattg gcgaggtgag ttataccggc | 1140 |
| ttacacggcg ctaaccgcat ggcctcgaat tcattgctgg agtgtctggt ctatggctgg | 1200 |
| tcggcggcgg aagatatcac cagacgtatg ccttatgccc acgacatcag tacgttaccg | 1260 |
| ccgtgggatg aaagccgcgt tgagaaccct gacgaacggg tagtaattca gcataactgg | 1320 |
| cacgagctac gtctgtttat gtgggattac gttggcattg tgcgcacaac gaagcgcctg | 1380 |
| gaacgcgccc tgcggcggat aaccatgctc caacaagaaa tagacgaata ttacgcccat | 1440 |
| ttccgcgtct caaataattt gctggagctg cgtaatctgg tacaggttgc cgagttgatt | 1500 |
| gttcgctgtg caatgatgcg taaagagagt cgggggttgc atttcacgct ggattatccg | 1560 |
| gaactgctca cccattccgg tccgtcgatc cttcccccg gcaatcatta cataaacaga | 1620 |
| taa | 1623 |

<210> SEQ ID NO 14
<211> LENGTH: 1044
<212> TYPE: DNA
<213> ORGANISM: Escherichia coli
<220> FEATURE:

```
<221> NAME/KEY: gene
<222> LOCATION: (1)..(1044)
<223> OTHER INFORMATION: nadA ORF

<400> SEQUENCE: 14
atgagcgtaa tgtttgatcc agacacggcg atttatcctt tccccccgaa gccgacgccg      60
ttaagcattg atgaaaaagc gtattaccgc gagaagataa aacgtctgct aaaagaacgt     120
aatgcggtga tggttgccca ctactatacc gatcccgaaa ttcaacaact ggcagaagaa     180
accggtggct gtatttctga ttctctggaa atggcgcgct tcggtgcaaa gcatcccgct     240
tctactttgt tagtcgctgg ggtgagattt atgggagaaa ccgccaaaat tctcagtccg     300
gaaaaaacaa ttctgatgcc gacacttcag gctgaatgtt cactggatct cggctgccct     360
gttgaagaat ttaacgcatt ttgcgatgcc catcccgatc gtactgtcgt cgtctacgcc     420
aacacttctg ctgcggtaaa agcgcgcgca gattgggtgg taacttcaag cattgccgtc     480
gaacttattg atcatcttga tagtttgggt gaaaaaatca tctgggcacc cgacaaacat     540
ctggggcgtt acgtgcaaaa acagacgggt ggagacattc tatgctggca gggtgcctgt     600
attgtgcatg atgaatttaa gactcaggcg ttaacccgct tgcaagaaga atacccggat     660
gctgccatac tggtgcatcc agaatcacca caagctattg tcgatatggc ggatgcggtc     720
ggttccacca gtcaactgat cgctgctgcg aaaacattgc cacatcagag gcttattgtg     780
gcaaccgatc ggggtatttt ctacaaaatg cagcaggcgg tgccagataa agagttactg     840
gaagcaccaa ccgcaggtga gggtgcaacc tgccgcagct gcgcgcattg tccgtggatg     900
gccatgaatg gccttcaggc catcgcagag gcattagaac aggaaggaag caatcacgag     960
gttcatgttg atgaaaggct gcgagagagg gcgctggtgc cgctcaatcg tatgctggat    1020
tttgcggcta cactacgtgg ataa                                             1044

<210> SEQ ID NO 15
<211> LENGTH: 894
<212> TYPE: DNA
<213> ORGANISM: Escherichia coli W3110
<220> FEATURE:
<221> NAME/KEY: gene
<222> LOCATION: (1)..(894)
<223> OTHER INFORMATION: nadC ORF

<400> SEQUENCE: 15
atgccgcctc gccgctataa ccctgacacc cgacgtgacg agctgctgga acgcattaat      60
ctcgatatcc ccggcgcggt ggcccaggcg ctgcgggaag attttaggcgg aacagtcgat    120 gccaacaatg atattacggc aaaacttttta ccggaaaatt ctcgctctca tgccacggtg    180
atcacccgcg agaatggcgt cttttgcggc aaacgctggg ttgaagaggt gtttattcaa    240
ctggcaggcg acgatgtcac cataatctgg catgtggatg acggcgatgt catcaatgcc    300
aatcaatcct tgttcgaact tgaaggccca tcccgcgtgc tgttaacggg cgaacgcact    360
gcgcttaatt ttgtgcaaac cctttcagga gttgccagta aggtacgcca ctatgtcgaa    420
ttgctggaag gcaccaacac gcagttgttg gatacgcgca aaaccttacc cggcctgcgt    480
tcagctctga atacgcggt actttgcggc ggcgagcga atcaccgtct ggggctttct    540
gatgccttcc tgatcaaaga aaaccatatt attgcctccg gctcagtgcg ccaggcggtc    600
gaaaaagcgt cctggctgca cccggatgcg ccagtagaag tcgaagtaga gaatctggaa    660
gaacttgatg aagcccctgaa agcaggagcc gatatcatca tgctggataa cttcgaaaca    720
gaacagatgc gcgaagccgt caaacgcacc aacggcaagg cgctactgga agtgtctggc    780
```

```
aacgtcactg acaaaacact gcgtgaattt gccgaaacgg gcgtggactt tatctccgtc    840
ggtgcgctaa ctaaacacgt acaagcactc gacctttcaa tgcgttttcg ctaa          894

<210> SEQ ID NO 16
<211> LENGTH: 135
<212> TYPE: DNA
<213> ORGANISM: Artificial Sequence
<220> FEATURE:
<223> OTHER INFORMATION: Pro promoter

<400> SEQUENCE: 16
ctcgagcata gcattttat ccataagatt agcggatcta acctttacaa ttgtgagcgc    60
tcacaattat gatagattca attgtgagcg gataacaatt tcacacagaa ttcattaaag   120
aggagaaagg tacat                                                    135

<210> SEQ ID NO 17
<211> LENGTH: 294
<212> TYPE: DNA
<213> ORGANISM: Escherichia coli W3110
<220> FEATURE:
<221> NAME/KEY: promoter
<222> LOCATION: (1)..(294)
<223> OTHER INFORMATION: cysK promoter

<400> SEQUENCE: 17
ccagcctgtt tacgatgatc ccgctgctta atctgttcat catgcccgtt gccgtttgtg    60
gcgcgacggc gatgtgggtc gattgctatc gcgataaaca cgcgatgtgg cggtaacaat   120
ctaccggtta ttttgtaaac cgtttgtgtg aaacaggggt ggcttatgcc gccccttatt   180
ccatcttgca tgtcattatt tcccttctgt atatagatat gctaaatcct tacttccgca   240
tattctctga gcgggtatgc tacctgttgt atcccaattt catacagtta agga         294

<210> SEQ ID NO 18
<211> LENGTH: 5900
<212> TYPE: DNA
<213> ORGANISM: Artificial Sequence
<220> FEATURE:
<223> OTHER INFORMATION: Plasmid vector (pPro-nadBA)

<400> SEQUENCE: 18
ctcgagcata gcattttat ccataagatt agcggatcta acctttacaa ttgtgagcgc    60
tcacaattat gatagattca attgtgagcg gataacaatt tcacacagaa ttcattaaag   120
aggagaaagg tacatatgaa tactctccct gaacattcat gtgacgtgtt gattatcggt   180
agcggcgcag ccggactttc actggcgcta cgcctggctg accagcatca ggtcatcgtt   240
ctaagtaaag gccggtaac ggaaggttca acatttatg cccagggcgg tattgccgcc    300
gtgtttgatg aaactgacag cattgactcg catgtggaag acacattgat gccggggct   360 ggtatttgcg atcgccatgc agttgaattt gtcgccagca atgcacgatc ctgtgtgcaa   420
tggctaatcg accaggggt gttgtttgat acccacattc aaccgaatgg cgaagaaagt   480
taccatctga cccgtgaagg tggacatagt caccgtcgta ttcttcatgc cgccgacgcc   540
accggtagag aagtagaaac cacgctggtg agcaaggcgc tgaaccatcc gaatattcgc   600
gtgctggagc gcagcaacgc ggttgatctg attgtttctg acaaaattgg cctgccgggc   660
acgcgacggt tgttggcgc gtgggtatgg aaccgtaata agaaacggt ggaaacctgc    720 cacgcaaaag cggtggtgct ggcaaccggc ggtgcgtcga aggtttatca gtacaccacc   780
```

```
aatccggata tttcttctgg cgatggcatt gctatggcgt ggcgcgcagg ctgccgggtt      840
gccaatctcg aatttaatca gttccaccct accgcgctat atcacccaca ggcacgcaat      900
ttcctgttaa cagaagcact gcgcggcgaa ggcgcttatc tcaagcgccc ggatggtacg      960
cgttttatgc ccgattttga tgagcgcggc gaactggccc cgcgcgatat tgtcgcccgc     1020
gccattgacc atgaaatgaa acgcctcggc gcagattgta tgttccttga tatcagccat     1080
aagcccgccg attttattcg ccagcatttc ccgatgattt atgaaaagct gctcgggctg     1140
gggattgatc tcacacaaga accggtaccg attgtgcctg ctgcacatta tacctgcggt     1200
ggtgtaatgg ttgatgatca tgggcgtacg gacgtcgagg gcttgtatgc cattggcgag     1260
gtgagttata ccggcttaca cggcgctaac cgcatggcct cgaattcatt gctggagtgt     1320
ctggtctatg gctggtcggc ggcggaagat atcaccagac gtatgcctta tgcccacgac     1380
atcagtacgt taccgccgtg ggatgaaagc cgcgttgaga cccctgacga acgggtagta     1440
attcagcata actggcacga gctacgtctg tttatgtggg attacgttgg cattgtgcgc     1500
acaacgaagc gcctggaacg cgccctgcgg cggataacca tgctccaaca agaaatagac     1560
gaatattacg cccatttccg cgtctcaaat aatttgctgg agctgcgtaa tctggtacag     1620
gttgccgagt tgattgttcg ctgtgcaatg atgcgtaaag agagtcgggg gttgcatttc     1680
acgctggatt atccggaact gctcacccat tccggtccgt cgatccttc ccccggcaat     1740 cattacataa acagataaaa agcctgggtc agcgccgtat acgcttcgga atagttctgg     1800
tctggcccac gaatgactaa gcgatcgcta aagcattctc ccgcctgcgg ggagaatgcc     1860
agcagcaccc gatgcggcag tcgcgcttcg ttttccgcca catccgtccg caaacgtaaa     1920
tgccagccca tgcttaatgc cagctccgta aaaccattac caatctgctc tggcagcact     1980
acgcagaaaa atccctcttc ggtaatgcac tccgccgcac aggtcagcaa cgatgggtga     2040
tcaagcgtag tggtataggg atccccagcc tgtttacgat gatcccgctg cttaatctgt     2100
tcatcatgcc cgttgccgtt tgtggcgcga cggcgatgtg ggtcgattgc tatcgcgata     2160
aacacgcgat gtggcggtaa caatctaccg gttattttgt aaaccgtttg tgtgaaacag     2220
gggtggctta tgccgcccct tattccatct tgcatgtcat tatttccctt ctgtatatag     2280
atatgctaaa tccttacttc cgcatattct ctgagcgggt atgctacctg ttgtatccca     2340
atttcataca gttaaggagg gcccatgagc gtaatgtttg atccagacac ggcgatttat     2400
cctttccccc cgaagccgac gccgttaagc attgatgaaa aagcgtatta ccgcgagaag     2460
ataaaacgtc tgctaaaaga acgtaatgcg gtgatggttg cccactacta taccgatccc     2520
gaaattcaac aactggcaga agaaaccggt ggctgtattt ctgattctct ggaaatggcg     2580
cgcttcggtg caaagcatcc cgcttctact ttgttagtcg ctggggtgag atttatggga     2640
gaaaccgcca aaattctcag tccggaaaaa acaattctga tgccgacact tcaggctgaa     2700
tgttcactgg atctcggctg ccctgttgaa gaatttaacg cattttgcga tgcccatccc     2760
gatcgtactg tcgtcgtcta cgccaacact tctgctgcgg taaaagcgcg cgcagattgg     2820
gtggtaactt caagcattgc cgtcgaactt attgatcatc ttgatagttt gggtgaaaaa     2880
atcatctggg cacccgacaa acatctgggg cgttacgtgc aaaaacagac gggtggagac     2940
attctatgct ggcagggtgc ctgtattgtg catgatgaat ttaagactca ggcgttaacc     3000
cgcttgcaag aagaataccc ggatgctgcc atactggtgc atccagaatc accacaagct     3060
attgtcgata tggcggatgc ggtcggttcc accagtcaac tgatcgctgc tgcgaaaaca     3120
ttgccacatc agaggcttat tgtggcaacc gatcggggta ttttctacaa aatgcagcag     3180
```

```
gcggtgccag ataaagagtt actggaagca ccaaccgcag gtgagggtgc aacctgccgc    3240
agctgcgcgc attgtccgtg gatggccatg aatggccttc aggccatcgc agaggcatta    3300
gaacaggaag gaagcaatca cgaggttcat gttgatgaaa ggctgcgaga gagggcgctg    3360
gtgccgctca atcgtatgct ggattttgcg gctacactac gtggataacg aataataagg    3420
cgtaacgtta cgctttgggg gaaagatgga tttttttagt gtgcagaata tcctggtaca    3480
tataccaata ggggcaggcg gttatgatct ctcatggatc gaagcggtag gcacgagcgg    3540
ccgcttaatt aattaatcta gaggcatcaa ataaaacgaa aggctcagtc gaaagactgg    3600
gcctttcgtt ttatctgttg tttgtcggtg aacgctctcc tgagtaggac aaatccgccg    3660
ccctagacct aggggatata ttccgcttcc tcgctcactg actcgctacg ctcggtcgtt    3720
cgactgcggc gagcggaaat ggcttacgaa cggggcggag atttcctgga agatgccagg    3780
aagatactta acagggaagt gagagggccg cggcaaagcc gttttttccat aggctccgcc    3840 cccctgacaa gcatcacgaa atctgacgct caaatcagtg gtggcgaaac ccgacaggac    3900
tataaagata ccaggcgttt ccccctggcg gctccctcgt gcgctctcct gttcctgcct    3960
ttcggtttac cggtgtcatt ccgctgttat ggccgcgttt gtctcattcc acgcctgaca    4020
ctcagttccg ggtaggcagt tcgctccaag ctggactgta tgcacgaacc ccccgttcag    4080
tccgaccgct gcgccttatc cggtaactat cgtcttgagt ccaacccgga agacatgca    4140 aaagcaccac tggcagcagc cactggtaat tgatttagag gagttagtct tgaagtcatg    4200
cgccggttaa ggctaaactg aaaggacaag ttttggtgac tgcgctcctc caagccagtt    4260
acctcggttc aaagagttgg tagctcagag aaccttcgaa aaaccgccct gcaaggcggt    4320
tttttcgttt tcagagcaag agattacgcg cagaccaaaa cgatctcaag aagatcatct    4380
tattaatcag ataaaatatt actagatttc agtgcaattt atctcttcaa atgtagcacc    4440
tgaagtcagc cccatacgat ataagttgtt actagtgctt ggattctcac caataaaaaa    4500
cgcccggcgg caaccgagcg ttctgaacaa atccagatgg agttctgagg tcattactgg    4560
atctatcaac aggagtccaa gcgagctctc gaaccccaga gtcccgctca gaagaactcg    4620
tcaagaaggc gatagaaggc gatgcgctgc gaatcgggag cggcgatacc gtaaagcacg    4680
aggaagcggt cagcccattc gccgccaagc tcttcagcaa tatcacgggt agccaacgct    4740
atgtcctgat agcggtccgc cacacccagc cggccacagt cgatgaatcc agaaaagcgg    4800
ccattttcca ccatgatatt cggcaagcag gcatcgccat gggtcacgac gagatcctcg    4860
ccgtcgggca tgcgcgcctt gagcctggcg aacagttcgg ctggcgcgag ccctgatgc    4920 tcttcgtcca gatcatcctg atcgacaaga ccggcttcca tccgagtacg tgctcgctcg    4980
atgcgatgtt tcgcttggtg gtcgaatggg caggtagccg gatcaagcgt atgcagccgc    5040
cgcattgcat cagccatgat ggatactttc tcggcaggag caaggtgaga tgacaggaga    5100
tcctgccccg gcacttcgcc caatagcagc cagtcccttc ccgcttcagt gacaacgtcg    5160
agcacagctg cgcaaggaac gcccgtcgtg gccagccacg atagccgcgc tgcctcgtcc    5220
tgcagttcat tcagggcacc ggacaggtcg gtcttgacaa aaagaaccgg gcgcccctgc    5280
gctgacagcc ggaacacggc ggcatcagag cagccgattg tctgttgtgc ccagtcatag    5340
ccgaatagcc tctccaccca gcggccgga gaacctgcgt gcaatccatc ttgttcaatc    5400
atgcgaaacg atcctcatcc tgtctcttga tcagatcttg atccctgcg ccatcagatc    5460 cttggcggca agaaagccat ccagtttact ttgcagggct tcccaacctt accagagggc    5520
```

```
gccccagctg gcaattccga cgtctgtgtg gaattctcgg acaccgagga gaatgtcaag    5580
aggcgaacac acaacgtctt ggagcgccag aggaggaacg agctaaaacg gagctttttt    5640
gccctgcgtg accagatccc ggagttggaa acaatgaaa aggcccccaa ggtagttatc     5700
cttaaaaaag ccacagcata catcctgtcc gtccaagcag aggagcaaaa gctcatttct    5760
gaagaggact tgttgcggaa acgacgagaa cagttgaaac acaaacttga acagctacgg    5820
aactcttgtg cgtaaggaaa agtaaggaaa acgattcctt ctaacagaaa tgtcctgagc    5880
aatcacctat gaactgtcga                                                5900
```

<210> SEQ ID NO 19
<211> LENGTH: 540
<212> TYPE: PRT
<213> ORGANISM: Escherichia coli W3110
<220> FEATURE:
<221> NAME/KEY: PEPTIDE
<222> LOCATION: (1)..(540)
<223> OTHER INFORMATION: NadB - aspartate oxidase

<400> SEQUENCE: 19

```
Met Asn Thr Leu Pro Glu His Ser Cys Asp Val Leu Ile Ile Gly Ser
  1               5                  10                  15

Gly Ala Ala Gly Leu Ser Leu Ala Leu Arg Leu Ala Asp Gln His Gln
             20                  25                  30

Val Ile Val Leu Ser Lys Gly Pro Val Thr Glu Gly Ser Thr Phe Tyr
         35                  40                  45

Ala Gln Gly Gly Ile Ala Ala Val Phe Asp Glu Thr Asp Ser Ile Asp
     50                  55                  60

Ser His Val Glu Asp Thr Leu Ile Ala Gly Ala Gly Ile Cys Asp Arg
 65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285
```

-continued

```
Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
            325                 330                 335

Ile Asp Leu Thr Gln Glu Pro Val Pro Ile Val Pro Ala Ala His Tyr
                340                 345                 350

Thr Cys Gly Gly Val Met Val Asp Asp His Gly Arg Thr Asp Val Glu
            355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
            405                 410                 415

Ser Thr Leu Pro Pro Trp Asp Glu Ser Arg Val Glu Asn Pro Asp Glu
        420                 425                 430

Arg Val Val Ile Gln His Asn Trp His Glu Leu Arg Leu Phe Met Trp
    435                 440                 445

Asp Tyr Val Gly Ile Val Arg Thr Thr Lys Arg Leu Glu Arg Ala Leu
    450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
            485                 490                 495

Ala Glu Leu Ile Val Arg Cys Ala Met Met Arg Lys Glu Ser Arg Gly
        500                 505                 510

Leu His Phe Thr Leu Asp Tyr Pro Glu Leu Leu Thr His Ser Gly Pro
    515                 520                 525

Ser Ile Leu Ser Pro Gly Asn His Tyr Ile Asn Arg
    530                 535                 540
```

<210> SEQ ID NO 20
<211> LENGTH: 347
<212> TYPE: PRT
<213> ORGANISM: Escherichia coli W3110
<220> FEATURE:
<221> NAME/KEY: PEPTIDE
<222> LOCATION: (1)..(347)
<223> OTHER INFORMATION: NadA - quinolinate sythase

<400> SEQUENCE: 20

```
Met Ser Val Met Phe Asp Pro Asp Thr Ala Ile Tyr Pro Phe Pro Pro
  1               5                  10                  15

Lys Pro Thr Pro Leu Ser Ile Asp Glu Lys Ala Tyr Tyr Arg Glu Lys
             20                  25                  30

Ile Lys Arg Leu Leu Lys Glu Arg Asn Ala Val Met Val Ala His Tyr
         35                  40                  45

Tyr Thr Asp Pro Glu Ile Gln Gln Leu Ala Glu Glu Thr Gly Gly Cys
     50                  55                  60

Ile Ser Asp Ser Leu Glu Met Ala Arg Phe Gly Ala Lys His Pro Ala
 65                  70                  75                  80

Ser Thr Leu Leu Val Ala Gly Val Arg Phe Met Gly Glu Thr Ala Lys
                 85                  90                  95
```

```
Ile Leu Ser Pro Glu Lys Thr Ile Leu Met Pro Thr Leu Gln Ala Glu
            100                 105                 110

Cys Ser Leu Asp Leu Gly Cys Pro Val Glu Glu Phe Asn Ala Phe Cys
        115                 120                 125

Asp Ala His Pro Asp Arg Thr Val Val Tyr Ala Asn Thr Ser Ala
        130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
                165                 170                 175

Pro Asp Lys His Leu Gly Arg Tyr Val Gln Lys Gln Thr Gly Gly Asp
            180                 185                 190

Ile Leu Cys Trp Gln Gly Ala Cys Ile Val His Asp Glu Phe Lys Thr
        195                 200                 205

Gln Ala Leu Thr Arg Leu Gln Glu Glu Tyr Pro Asp Ala Ala Ile Leu
    210                 215                 220

Val His Pro Glu Ser Pro Gln Ala Ile Val Asp Met Ala Asp Ala Val
225                 230                 235                 240

Gly Ser Thr Ser Gln Leu Ile Ala Ala Lys Thr Leu Pro His Gln
                245                 250                 255

Arg Leu Ile Val Ala Thr Asp Arg Gly Ile Phe Tyr Lys Met Gln Gln
            260                 265                 270

Ala Val Pro Asp Lys Glu Leu Glu Ala Pro Thr Ala Gly Glu Gly
            275                 280                 285

Ala Thr Cys Arg Ser Cys Ala His Cys Pro Trp Met Ala Met Asn Gly
    290                 295                 300

Leu Gln Ala Ile Ala Glu Ala Leu Glu Gln Glu Gly Ser Asn His Glu
305                 310                 315                 320

Val His Val Asp Glu Arg Leu Arg Glu Arg Ala Leu Val Pro Leu Asn
                325                 330                 335

Arg Met Leu Asp Phe Ala Ala Thr Leu Arg Gly
            340                 345

<210> SEQ ID NO 21
<211> LENGTH: 297
<212> TYPE: PRT
<213> ORGANISM: Escherichia coli W3110
<220> FEATURE:
<221> NAME/KEY: PEPTIDE
<222> LOCATION: (1)..(297)
<223> OTHER INFORMATION: NadC - quinolinate phosphoribosyltransferase

<400> SEQUENCE: 21

Met Pro Pro Arg Arg Tyr Asn Pro Asp Thr Arg Arg Asp Glu Leu Leu
1               5                   10                  15

Glu Arg Ile Asn Leu Asp Ile Pro Gly Ala Val Ala Gln Ala Leu Arg
            20                  25                  30

Glu Asp Leu Gly Gly Thr Val Asp Ala Asn Asn Asp Ile Thr Ala Lys
        35                  40                  45

Leu Leu Pro Glu Asn Ser Arg Ser His Ala Thr Val Ile Thr Arg Glu
    50                  55                  60

Asn Gly Val Phe Cys Gly Lys Arg Trp Val Glu Val Phe Ile Gln
65                  70                  75                  80

Leu Ala Gly Asp Asp Val Thr Ile Ile Trp His Val Asp Asp Gly Asp
                85                  90                  95

Val Ile Asn Ala Asn Gln Ser Leu Phe Glu Leu Glu Gly Pro Ser Arg
```

-continued

```
              100                 105                 110
Val Leu Leu Thr Gly Glu Arg Thr Ala Leu Asn Phe Val Gln Thr Leu
            115                 120                 125

Ser Gly Val Ala Ser Lys Val Arg His Tyr Val Glu Leu Leu Glu Gly
            130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Ala Asn His Arg
            165                 170                 175

Leu Gly Leu Ser Asp Ala Phe Leu Ile Lys Glu Asn His Ile Ile Ala
            180                 185                 190

Ser Gly Ser Val Arg Gln Ala Val Glu Lys Ala Ser Trp Leu His Pro
            195                 200                 205

Asp Ala Pro Val Glu Val Glu Val Glu Asn Leu Glu Glu Leu Asp Glu
            210                 215                 220

Ala Leu Lys Ala Gly Ala Asp Ile Ile Met Leu Asp Asn Phe Glu Thr
225                 230                 235                 240

Glu Gln Met Arg Glu Ala Val Lys Arg Thr Asn Gly Lys Ala Leu Leu
                245                 250                 255

Glu Val Ser Gly Asn Val Thr Asp Lys Thr Leu Arg Glu Phe Ala Glu
                260                 265                 270

Thr Gly Val Asp Phe Ile Ser Val Gly Ala Leu Thr Lys His Val Gln
            275                 280                 285

Ala Leu Asp Leu Ser Met Arg Phe Arg
            290                 295
```

METHOD FOR THE PREPARATION OF NICOTINIC ACID

CROSS-REFERENCE TO RELATED APPLICATION

This application is the U.S. national phase of PCT Application No. PCT/KR2012/000370 filed on Jan. 16, 2012, which claims priority to Korean Patent Application No. 10-2011-0004093 filed on Jan. 14, 2011, the disclosures of which are incorporated in their entirety by reference herein.

SEQUENCE LISTING

The text file is Sequence_Listing_PCT_KR2012_000370.txt, created Jul. 5, 2013, and of size 26 KB, filed therewith, is hereby incorporated by reference.

TECHNICAL FIELD

The present invention relates to a method for preparing nicotinic acid via incubation of microorganisms having an ability to produce quinolinic acids and decarboxylation of the quinolinic acids obtained therefrom.

BACKGROUND ART

Nicotinic acid is an oxide of nicotine and is extensively present in animal and plant bodies as a water-soluble vitamin, which is also called vitamin B complex, niacin or vitamin B3. Deficiency of nicotinic acid may result in pellagra disease or neuropathies. Nicotinic acid is generally present in the form of nicotinic acid amide co-enzyme (NAD, NADP) in the living body, and participates in the oxidation-reduction reaction.

Nicotinic acid as usefully utilized in food and medicinal products can be prepared by means of chemical synthetic method or biological producing method. Chemical synthesis of nicotinic acid has been generally accomplished through oxidation using 3-picolne as an oxidizing catalyst. Specifically, 2-methylpentanediamine (MPDA) is subjected to hyperthermal reaction (280 to 360° C.) by means of a catalyst to synthesize 3-picoline, and then 3-picoline is subjected to ammoxidation to produce 3-cyanopyrine, which is then hydrolyzed to synthesize niacinamide or nicotinic acid. Alternatively, nicotinic acid can be directly synthesized from 3-picoline through selective oxidation (Applied Catalysis A: General 280 (2005) 75-82). However, because chemical synthesis results in large quantities of toxic wastes including the catalyst, there is a need of thorough management and great expenses are required for disposal of wastes. In order to solve such problem the method for synthesizing niacin from 3-cyanopyridine using an enzyme has been developed. However, this method also has similar problems due to the use of 3-cyanopyrine which causes a generation of wastes in large quantities. Further, because pyrimidine used as a precursor has various derivatives, and thus, suffers from a great fluctuation in the supply and price thereof, this method may cause instability of niacin price.

In addition, other methods for producing nicotinic acid from quinolinic acid have been disclosed. Chinese Patent CN101353322C discloses the method for synthesis of nicotinic acid using quinolinic acid as the substrate through hydrothermal decarboxylation. The method for producing nicotinic acid proceeds by mixing quinolinic acid with deionized hot water in the ratio of 2:1 to 5:1 and then allowing the mixture to react at a high temperature of 150 to 250° C. and high pressure of 1 to 2 MPa for 5 to 60 minutes (Ind. Eng. Chem. Res. 2009, 48, 10467-10471). This method has an advantage in that no side product of the catalyst is produced, while it has also the problems that the reaction conditions are high temperature and high pressure of 150 to 250° C. and 2 MPa require high energy. All the established chemical synthetic methods use non-renewable materials derived from petroleum as the raw material, and therefore, are greatly influenced by environmental problems or the unit price of petroleum extraction.

In order to solve such problems involved in the chemical synthesis methods, methods for biologically producing nicotinic acid by means of renewable carbohydrate-derived materials has been studied. Biological production of nicotinic acid has been accomplished mainly through two kinds of synthetic pathway. The first one is a pathway to produce quinolinic acid from tryptophan as a starting material, and then biologically synthesize nicotinic acid from the quinolinic acid, and the other is a pathway to produce quinolinic acid from aspartic acid as a starting material, and then biologically synthesize nicotinic acid from the quinolinic acid. In general, eukaryotes biologically synthesize nicotinic acid through the pathway to synthesize nicotinic acid from tryptophan as the starting material, while prokaryotes utilize the pathway to synthesize nicotinic acid from aspartic acid as the starting material as the main pathway. Both pathways comprise quinolinic acid as the intermediate, and synthesize nicotinic acid by the action of quinolinate phosphoribosyltransferase (nadC), nicotinate-mononucleotide adenylyltransferase (nadD), NAD synthetase (nadE), NMN adenylyltransferase (nadR) and nicotinamidase (pncA) from quinolinic acid.

The method for biological production of nicotinic acid utilizing recombinant *Escherichia coli* or *Corynebacterium glutamicum*, which produce nicotinic acid through the aspartic acid pathway, has been reported. U.S. Pat. Nos. 6,692,946 and 6,689,587 disclose the methods for producing nicotinic acid by separating the nadA gene and nadC gene, which encode quinolinate synthetase and quinolinate phosphoribosyltransferase, respectively, from the *Corynebacterium glutamicum* (ATCC 13032) strain, and then, incubating host cells which over-express such genes. The amount of nicotinic acid produced by the methods for biological production of nicotinic acid as disclosed in said US patents is very low, below 100 mg/L. It is considered that the causes of this low production include transcriptional suppression by NadR, which is an NAD-related transcriptional repressor of nadB as the gene coding for aspartate oxidase and nadA as the gene coding for quinolinate synthetase (Gerasimova AV (2005). J Bioinform Comput Biol 3(4); 1007-19.), feedback inhibition of aspartate oxidase and NAD synthetase with NAD (Biol Chem Hoppe Seyler. 1990 March; 371(3):239-48), complexity of the reaction including the steps by NadB, NadA, NadC, as well as NadD, NadE, NadR and PncA, and the like.

The methods for biological production of nicotinic acid have the disadvantages in that the production yield of nicotinic acid is very low due to inhibition of the expression of enzymes involved in said biosynthetic pathways, feedback inhibition and complexity of reaction.

DISCLOSURE OF INVENTION

Technical Problem

In light of the above-mentioned technical challenges, the present inventors have conducted a study to solve the problems involved in the chemical synthesis and biological production methods for nicotinic acid, and to improve the production yield of nicotinic acid, and thus, complete the present method for producing nicotinic acid in a high yield through the combination of a biological production method and a chemical synthesis method.

Solution to Problem

The purpose of the present invention is to provide a method for the preparation of nicotinic acid, which comprises the step of obtaining a culture solution containing quinolinic acid by incubating a microorganism having an ability to produce quinolinic acid, and the step of adding an acid to the culture solution and conducting a decarboxylation reaction.

Advantageous Effects of Invention

By replacing the prior process for preparing nicotinic acid via chemical synthesis with the process for producing quinolinic acid via fermentation, and providing the process for converting quinolinic acid into nicotinic acid through the addition of acid to the culture solution containing quinolinic acid and decarboxylation reaction, the present invention can solve the problems involved in the prior methods, including the catalyst side products, the requirement of high energy and environmental problem caused by use of non-renewable resources in chemical synthesis, and the low yield in biological production, thereby producing nicotinic acid in a more environmental-friendly and efficient manner.

BEST MODE FOR CARRYING OUT THE INVENTION

Figure 1:
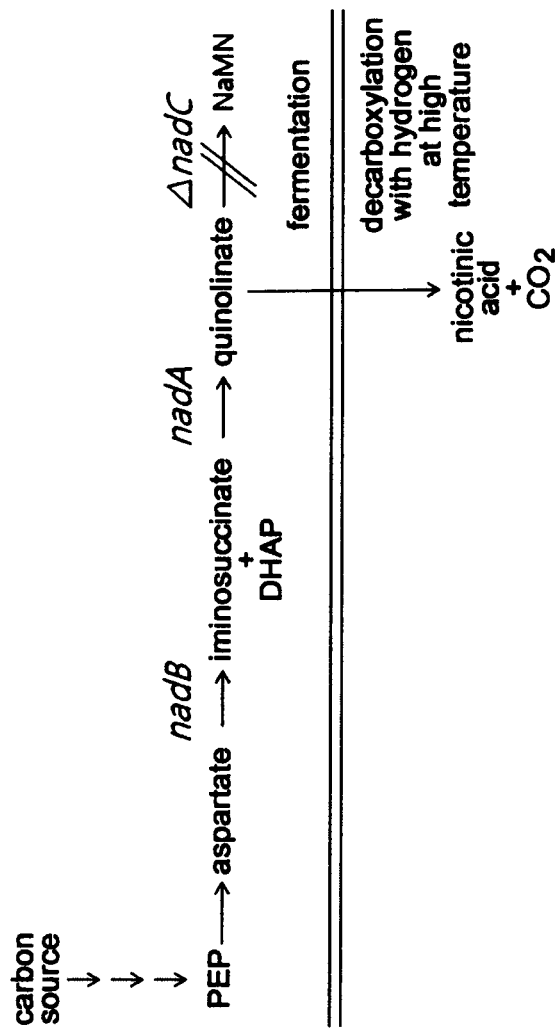
FIG. 1 shows a pathway for the preparation of nicotinic acid in the method for preparing nicotinic acid according to one embodiment of the present invention.

In one aspect, the present invention provides a method for the preparation of nicotinic acid, which comprises the step of obtaining a culture solution containing quinolinic acid by incubating a microorganism having an ability to produce quinolinic acid, and the step of adding an acid to the culture solution and conducting a decarboxylation reaction.

As used herein, the term "microorganism having an ability to produce quinolinic acid" denotes microorganisms which can produce quinolinic acid from a carbon source in a culture medium and accumulate them.

As used herein, the term "decarboxylation" denotes a reaction to produce nicotinic acid by decarboxylation of the reactant, i.e. quinolinic acid.

In one embodiment of the present invention, the microorganism having an ability to produce quinolinic acid can be microorganism whose ability to produce quinolinic acid is improved through weakening or removal of quinolinate phosphoribosyltransferase activity and enhancement of aspartate oxidase and quinolinate synthetase activities.

In another embodiment of the present invention, quinolinate phosphoribosyl-transferase can have the amino acid sequence equivalent to SEQ ID NO: 21 or a sequence having a high homology thereto; aspartate oxidase can have the amino acid sequence equivalent to SEQ ID NO: 19 or a sequence having a high homology thereto; and quinolinate synthetase can have the amino acid sequence equivalent to SEQ ID NO: 20 or a sequence having a high homology thereto.

To improve the ability to produce quinolinic acid, it is required that microorganisms produce large quantities of quinolinic acid and quinolinic acid thus produced can be accumulated without being used in another pathway. Therefore, in the present invention, microorganism having an improved ability to produce quinolinic acid can be prepared by the way to remove or weaken the activity of quinolinate phosphoribosyltransferase, which acts on the decomposition pathway of quinolinic acid, the way to enhance the expression of aspartate oxidase and quinolinate synthetase, which act on the synthetic pathway of quinolinic acid, or the combination thereof.

In still another embodiment of the present invention, said weakening or removal of quinolinate phosphoribosyltransferase activity can be achieved by one or more way selected from the way to replace an endogenous gene coding for quinolinate phosphoribosyltransferase with a modified gene whose enzyme activity is weakened or removed, the way to replace an endogenous promoter for said gene with a promoter whose activity is weaker than that of the endogenous promoter, or the way to delete said gene from chromosome.

In still another embodiment of the present invention, said enhancement of aspartate oxidase and quinolinate synthetase activities can be achieved by one or more way selected from the way to increase the genomic copy number of intracellular genes coding for aspartate oxidase and quinolinate synthetase, the way to modify expression regulatory sequences of said genes, and the way to replace said gene with a modified gene whose enzyme activity is enhanced.

In yet another embodiment of the present invention, in order that quinolinic acid can be accumulated in the culture solution of microorganisms, the promoter portion of nadB as the gene coding for aspartate oxidase protein is substituted with a constitutive promoter, pPro, of SEQ ID NO: 16 to construct the constitutive expressible nadB gene, which is not suppressed by NadR as the transcriptional repressor to suppress the expression of nadB gene with intracellular NAD level, in the form of a plasmid, and said plasmid is then introduced into microorganisms to induce over-expression of aspartate oxidase.

In another embodiment of the present invention, aspartate oxidase can have the amino acid sequence of SEQ ID NO: 19. The sequence of gene nadB encoding said enzyme can be obtained from the genome sequence (gi: GI:89109380) of *Escherichia coli* as disclosed in Mol Syst Biol. 2006; 2:2006.0007. Epub 2006 Feb. 21, or the database available from the National Center for Biotechnology Information (NCBI) and the DNA Data Bank for Japan (DDBJ).

Aspartate oxidase has an activity to oxidize aspartic acid to iminosuccinic acid, as shown in the following reaction scheme:

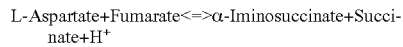
L-Aspartate+Fumarate<=>α-Iminosuccinate+Succinate+H$^+$

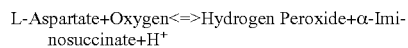
L-Aspartate+Oxygen<=>Hydrogen Peroxide+α-Iminosuccinate+H$^+$

Therefore, if the activity of aspartate oxidase is enhanced, accumulation of iminosuccinic acid, as the precursor of quinolinic acid in cells can be increased, thereby increasing the production of quinolinic acid.

In still another embodiment of the present invention, in order to increase the accumulation of quinolinic acid, the promoter of the gene coding for quinolinate synthetase protein is substituted with a stronger promoter, pCysK of SEQ ID NO: 17, to construct the constitutive expressible nadA gene, which is not suppressed by NadR, as the transcriptional repressor to suppress the expression of nadA gene with intracellular NAD level, in the form of a plasmid, and said plasmid is then introduced into microorganisms to induce over-expression of quinolinate synthetase.

In still another embodiment of the present invention, quinolinate synthetase can have the amino acid sequence of SEQ ID NO: 20. The sequence of gene nadA encoding said enzyme can be obtained from the genome sequence (gi: GI: 89107601) of *Escherichia coli* as published in Mol Syst Biol. 2006; 2:2006.0007. Epub 2006 Feb. 21, or the database available from the National Center for Biotechnology Information (NCBI) and the DNA Data Bank for Japan (DDBJ).

Quinolinate synthetase has an activity to synthesize quinolinic acid from iminosuccinic acid, as shown in the following reaction scheme:

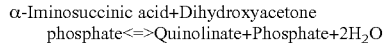

α-Iminosuccinic acid+Dihydroxyacetone
phosphate<=>Quinolinate+Phosphate+2H$_2$O

Therefore, if the expression of the gene encoding quinolinate synthetase or the activity of said enzyme is enhanced, the production of quinolinic acid in cells can be increased.

In microorganism having the ability to produce quinolinic acid, the activities of aspartate oxidase and quinolinate synthetase can be enhanced by substituting the endogenous promoters of genes coding for aspartate oxidase and quinolinate synthetase with a stronger promoter, or by introducing a mutation in the promoters to increase the activity thereof or increasing the copy number of said genes, respectively. For substitution with said stronger promoter, those generally known as being stronger promoters, including pTac, pTrc, pPro, pR, pL, pCJ1, pCysK, etc., can be used.

In still another embodiment of the present invention, the promoters of genes nadB and nadA participating in the biosynthesis of quinolinic acid can be substituted with a stronger promoter pPro or pCysK to prepare microorganism strains, which overexpress said genes thereby having an improved ability to produce quinolinic acid. As the promoter substituting for the endogenous promoter to increase the expression of said genes, promoters pPro and pCysK of SEQ ID NOs: 17 and 18, respectively, or a portion thereof can be used.

In addition, in order that microorganism can further accumulate quinolinic acid, the activity of quinolinate phosphoribosyltransferase, as the enzyme to convert quinolinic acid into nicotinate mononucleotide, which is located on the genome of microorganisms having the ability to produce quinolinic acid, can be removed. For this purpose, nadC as the gene coding for quinolinate phosphoribosyltransferase can be removed from the genome of microorganism by means of homologous recombination. The sequence of the gene nadC can be obtained from the genome sequence (gi: GI: 89106990) of *Escherichia coli* as published in Mol Syst Biol. 2006; 2:2006.0007. Epub 2006 Feb. 21, or the database available from the National Center for Biotechnology Information (NCBI) and the DNA Data Bank for Japan (DDBJ).

In still another embodiment of the present invention, said phosphoribosyltransferase can have the amino acid sequence of SEQ ID NO: 21.

Quinolinate phosphoribosyltransferase has an activity to synthesize nicotinate mononucleotide from quinolinic acid, as shown in the following reaction scheme. Therefore, if the gene having said activity is removed or the expression thereof is weakened, the production of quinolinic acid in cells can be increased.

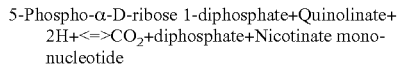

5-Phospho-α-D-ribose 1-diphosphate+Quinolinate+
2H+<=>CO$_2$+diphosphate+Nicotinate mononucleotide In still another embodiment of the present invention, microorganisms having an ability to produce quinolinic acid can be prokaryotic and eukaryotic microorganism strains. Said microorganisms having an ability to produce quinolinic acid can include, but are not be limited to, those belonging to *Enterbacter* genus, *Escherichia* genus, *Erwinia* genus, *Serratia* genus, *Providencia* genus, *Corynebacterium* genus or *Brevibacterium* genus.

Preferably, the microorganisms having an ability to produce quinolinic acid can be those belonging to *Escherichia* genus and more preferably, *Escherichia coli*.

In still another embodiment of the present invention, *E. coli* variant strain, TF4076 (KFCC 10718, Korean Patent Publication No. 92-8365), which produces L-threonine can be used as the parent strain for improving the ability to produce quinolinic acid. *Escherichia coli* TF4076 requires methionine or is resistant to threonine analogues (AHV: α-amino-β-hydroxy valeric acid), lysine analogues (AEC: S-(2-aminoethyl)-L-cysteine), isoleucine analogues (α-aminobutyric acid), methionine analogues (ethionine), etc.

Said *Escherichia coli* strain TF4076 can be modified to enhance the activities of aspartate oxidase and quinolinate synthetase, and to remove the activity of quinolinate phosphoribosyltransferase, thereby preparing the microorganism having an improved ability to produce quinolinic acid.

In yet another embodiment of the present invention, the microorganism having an ability to produce quinolinic acid can be *Escherichia coli*, which has the enhanced pathway for biosynthesis of quinolinic acid, through enhancement of the expression of genes coding for aspartate oxidase and quinolinate synthetase and removal and lowering of the activity of quinolinate phosphoribosyltransferase from the threonine-producing strain, TF4076 (KFCC 10718, Korean Patent Publication No. 92-8365), which has the enhanced pathway for biosynthesis of aspartic acid.

In still another embodiment of the present invention, microorganisms having an ability to produce quinolinic acid can be strains derived from lysine, threonine, isoleucine or methionine-producing microorganism strains of which the biosynthesis pathway for aspartic acid is enhanced.

A quinolinic acid-producing strain, the *Escherichia coli* CV01-0009 strain, which is prepared through enhancement of the expression of genes coding for aspartate oxidase and quinolinate synthetase and the removal and lowering of the activity of quinolinate phosphoribosyltransferase from *Escherichia coli* TF4076 strain, was deposited under the Budapest Treaty at the Korean Culture Center of Microorganisms (KCCM, located on Hongjae 1-Dong, Seodaemun-Gu, Seoul, Korea) with Accession No. KCCM11165P on Jan. 10, 2011.

The method for preparing nicotinic acid according to the present invention comprises the step of incubating the microorganism having an ability to produce quinolinic acid to obtain the culture solution containing quinolinic acid.

The incubation of microorganisms having an ability to produce quinolinic acid can be accomplished using a suitable culture medium under suitable culture conditions are as well-known in the relevant technical field. Such incubation procedures can be used by a person skilled in the relevant technical field and are readily adjusted according to the selected microorganism. The methods for incubation include, but are not limited to, batch, continuous and fed-batch cultures. Various methods for incubation of microorganisms have been disclosed in, for example, "Biochemical Engineering" by James M. Lee, Prentice-Hall International Editions, pp 138-176.

The culture medium to be used must meet the requirements of the particular strains in a suitable manner. Descriptions of culture media for various microorganisms are to be found in the handbook ["Manual of Methods for General Bacteriology" by the American Society for Bacteriology (Washington D.C., USA, 1981)]. The said culture media contains various carbon source, nitrogen source and microelement.

The useful carbon source may include sugars and carbohydrates such as glucose, saccharose, lactose, fructose, maltose, starch and cellulose, oils and fats such as soybean oil, sunflower oil, groundnut oil and coconut oil, fatty acids such as palmitic acid, stearic acid and linoleic acid, alcohols such as glycerol and ethanol, and organic acids such as acetic acid. Those substances may be used individually or in the form of a mixture.

The useful nitrogen source may include organic nitrogen-containing compounds such as peptones, yeast extract, meat extract, malt extract, corn steep liquor, soybean flour and urea, or inorganic compounds such as ammonium sulfate, ammonium chloride, ammonium phosphate, ammonium carbonate and ammonium nitrate. The nitrogen sources may be used individually or in the form of a mixture.

The useful phosphorus source may include potassium dihydrogen phosphate or dipotassium hydrogen phosphate or the corresponding sodium-containing salts. The culture medium can also contain metal salts such as magnesium sulfate or iron sulfate, which are necessary for growth. Finally, essential growth substances, such as amino acids and vitamins, may be used in addition to the above-mentioned substances. Suitable precursors may be also added to the culture medium. The mentioned substances may be added to the culture by continuous or batch type in a suitable manner during the cultivation.

Further, in order to control the pH value of the culture, basic compounds such as sodium hydroxide, potassium hydroxide, and ammonia or acid compounds such as phosphoric acid or sulfuric acid, are expediently used. In order to control the development of foam, an anti-foaming agent such as fatty acid polyglycol esters may be used. In order to maintain aerobic conditions, oxygen or oxygen-containing gas such as air is introduced into the culture. The temperature of the culture is normally from 20° C. to 45° C., and preferably from 25° C. to 40° C. The culture is continued until the expectative amount of the quinolinic acid has formed. That aim is normally achieved within a period of from 10 hours to 160 hours.

The method for preparing nicotinic acid according to the present invention comprises the step of conducting decarboxylation by adding the acid to the culture solution containing quinolinic acid.

More specifically, the culture solution containing quinolinic acid obtained from incubation of the microorganism having an ability to produce quinolinic acid is subjected to centrifugation or membrane filtration to remove the microorganisms. Then, to accelerate the decarboxylation reaction, the acid to provide hydrogen group is added to the culture solution containing quinolinic acid. Any acid can be used without restriction on the kind, as long as it can provide hydrogen group to the culture solution.

In one embodiment of the present invention, the culture solution containing quinolinic acid can be utilized without purification.

In another embodiment of the present invention, acids added to said culture solution can be hydrochloric acid or sulfuric acid.

In yet another embodiment of the present invention, after the addition of said acid, the culture solution can have the pH value of 5 or less.

In still another embodiment of the present invention, after the addition of said acid, the culture solution can have the pH value of 2 to 3.

In still another embodiment of the present invention, the decarboxylation of the culture solution can be conducted at a temperature ranges 100° C. to 150° C.

In still another embodiment of the present invention, the decarboxylation of the culture solution can be conducted at a temperature of 135° C.

In still another embodiment of the present invention, the decarboxylation of the culture solution can be conducted at a pressure ranges 0.1 MPa to 0.5 MPa.

In still another embodiment of the present invention, the decarboxylation of the culture solution can be conducted at a pressure of 0.2 MPa.

Upon conducting the decarboxylation under the high temperature and high pressure conditions for 1 to 3 hours after adding the acid to the fermentation solution containing quinolinic acid, quinolinic acid present in the culture solution is converted into nicotinic acid as shown in the following reaction scheme:

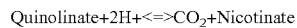

Quinolinate+2H+<=>$CO_2$+Nicotinate

The method for preparing nicotinic acid according to the present invention can further comprise steps for recovering and purifying nicotinic acid.

In the present invention, the recovery of nicotinic acid can be accomplished by any conventional method as known in the technical field to which the present invention belongs and which comprises the procedures for filtrating and crystallizing the culture solution.

Mode for the Invention

Hereinafter, it is intended to more specifically explain the present invention through Examples and Experimental Examples. However, these Examples are provided only to illustrate the present invention more in detail and the scope of the present invention is not limited by these Examples.

EXAMPLE 1

Preparation of Quinolinic Acid-Producing Strain 1-1. Construction of Plasmid for Expression of Aspartate Oxidase The gene nadB coding for aspartate oxidase was obtained through PCR using chromosomal DNA of *Escherichia coli* W3110 as the template. On the basis of the base sequence for the nadB gene (NCBI Registration No. "GI:89109380") of SEQ ID NO: 13 obtained from the GenBank of the National Institute of Health (NIH GenBank), the ATG region and ORF region containing the TAA in nadB gene could be amplified, and primers of SEQ ID NOs: 1 and 2 having the recognition sites of restriction enzymes NdeI and BamHI were synthesized.

PCR was conducted using chromosomal DNA of *Escherichia coli* W3110 as the template and oligonucleotides of SEQ ID NOs: 1 and 2 as the primer. PfuUltra™ DNA polymerase (Stratagene) was used as the polymerase, and PCR was conducted by repeating the cycle 30 times comprising denaturation at 96° C. for 30 seconds, annealing at 50° C. for 30 seconds and extension at 72° C. for 2 minutes. Thus, amplified gene of about 1.9 kb, which contains nadB gene and the recognition sites of restriction enzymes NdeI and BamHI was obtained.

The nadB gene obtained through said PCR procedures was treated with restriction enzymes NdeI and BamHI, and is then cloned by ligating into pProLar (CloneTech) vector treated with restriction enzymes NdeI and BamHI to ultimately construct pPro-nadB recombinant vector into which the nadB gene, of which the expression is controlled under pPro promoter as the constitutive promoter, is cloned.

1-2. Construction of Plasmid for Expression of Aspartate Oxidase and Quinolinate Synthetase The gene nadA coding for quinolinate synthetase was obtained through PCR using chromosomal DNA of *Escherichia coli* W3110 as the template. On the basis of the base sequence for the nadA gene (NCBI Registration No. "GI: 89107601") of SEQ ID NO: 14 obtained from the GenBank of the National Institute of Health (NIH GenBank), the ATG region and ORF region containing TAA in nadA gene could be amplified, and primers of SEQ ID NOs: 3 and 4 having the recognition sites of restriction enzymes ApaI and NotI were synthesized.

PCR was conducted using chromosomal DNA of *Escherichia coli* W3110 as the template and oligonucleotides of SEQ ID NOs: 3 and 4 as the primer. PfuUltra™ DNA polymerase (Stratagene) was used as the polymerase, and PCR was conducted by repeating the cycle 30 times comprising denaturation at 96° C. for 30 seconds, annealing at 50° C. for 30 seconds and extension at 72° C. for 2 minutes. Thus, amplified gene of about 1.0 kb, which contains nadA gene and the recognition sites of restriction enzymes ApaI and NotI was obtained.

cysK promoter was obtained through PCR using chromosomal DNA of *Escherichia coli* W3110 as the template. On the basis of the base sequence information (SEQ ID NO: 17) for promoter located within upstream 0.3 kb of cysK gene obtained from the GenBank of the National Institute of Health (NIH GenBank), primers of SEQ ID NOs: 5 and 6 having the recognition sites of restriction enzyme BamHI and ApaI were synthesized for ligating cysK promoter with said amplified nadA gene.

PCR was conducted using chromosomal DNA of *Escherichia coli* W3110 as the template and oligonucleotides of SEQ ID NOs: 5 and 6 as the primer. PfuUltra™ DNA polymerase (Stratagene) was used as the polymerase, and PCR was conducted by repeating the cycle 30 times comprising denaturation at 96° C. for 30 seconds, annealing at 50° C. for 30 seconds and extension at 72° C. for 1 minute. Thus, amplified gene of about 0.3 kb, which contains cysK promoter and the recognition sites of restriction enzymes BamHI and ApaI was obtained.

Figure 2:
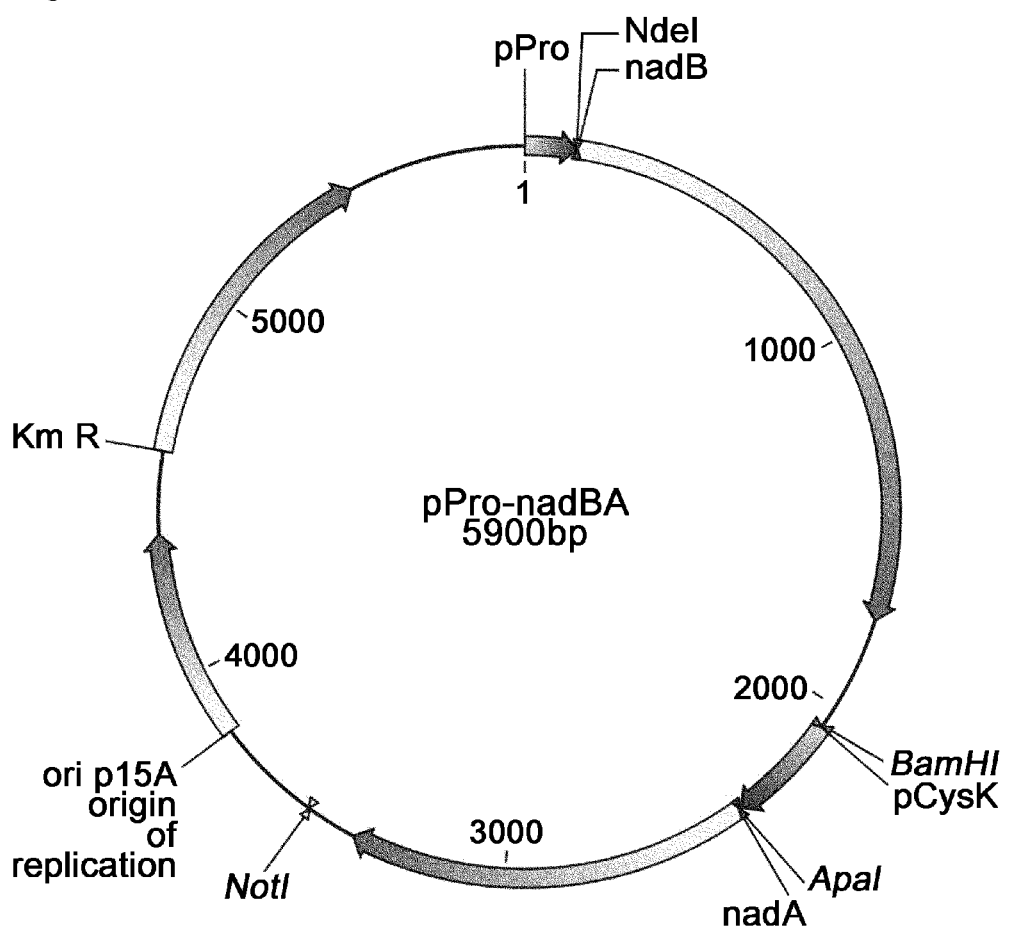
FIG. 2 shows the construction of pPro-nadBA as the expression plasmid of genes coding for aspartate oxidase and quinolinate synthetase.

The nadA gene obtained through said PCR procedures was treated with restriction enzymes ApaI and NotI, and amplified cysK promoter fragment was treated with ApaI and BamHI. The restriction enzyme treated nadA and cysK promoter fragments were cloned by ligating into the NotI and BamHI-treated pPro-nadB vector obtained from the above 1-1 to ultimately construct pPro-nadBA recombinant vector into which the nadB gene, of which the expression is controlled under pPro promoter as the constitutive promoter, and the nadA gene of which the expression is controlled by cysk gene promoter, are cloned. Constructed pPro-nadBA has the sequence of SEQ ID NO: 18. FIG. 2 shows the construction of pPro-nadBA as the expression plasmid of genes coding for aspartate oxidase and quinolinate synthetase.

1-3. Construction of Quinolinate Phosphoribosyltransferase-Deficient Strain

In the present example, the nadC gene involved in the decomposition pathway of quinolinic acid was obtained through PCR using chromosomal DNA of *Escherichia coli* TF4076 as the template. On the basis of the base sequence information of the nadC gene (NCBI Registration No. "GI: 89106990") obtained from the GenBank of the National Institute of Health (NIH GenBank), primers of SEQ ID NOs: 7 and 8 to amplify the downstream region of nadC gene, primers of SEQ ID NOs: 9 and 10 to amplify the upstream and downstream regions of nadC gene and loxpCm, and primers of SEQ ID NOs: 11 and 12 to amplify the upstream region of nadC gene, were synthesized.

PCR was conducted using chromosomal DNA of *Escherichia coli* TF4076 as the template and oligonucleotides of SEQ ID NOs: 7 and 8, and 11 and 12 as the primer to amplify the downstream and upstream regions of nadC gene of 0.5 kb and 0.3 kb, respectively. In addition, PCR was conducted using the plasmid vector containing loxpCm, pLoxpCat2 vector as the template, and oligonucleotides of SEQ ID NOs: 9 and 10 as the primer to amplify loxpCm gene having the sequence homologous to nadC gene on both ends of 1.0 kb. PfuUltra™ DNA polymerase (Stratagene) was used as the polymerase, and PCR was conducted by repeating the cycle 30 times comprising denaturation at 96° C. for 30 seconds, annealing at 53° C. for 30 seconds and extension at 72° C. for 1 minute. Then, nadC-upstream fragment, nadC-downstream fragment, and loxpCm section obtained from said PCR reactions were used as template to conduct PCR under PCR conditions including 10 repetition of the cycle comprising denaturation at 96° C. for 60 seconds, annealing at 50° C. for 60 seconds and extension at 72° C. for 1 minute, and 20 repetition of said cycle after addition of primers of SEQ ID NOs: 7 and 12. Thus, a nadC deficient cassette containing the upstream region of nadC gene-loxpCm-downstream region of nadC gene of 1.8 kb was obtained.

*Escherichia coli* TF4076 containing pKD46 as lambda red recombinase expression vector was transformed with the nadC deficient cassette by means of electroporation, and then the strain was smeared on LB (Luria-Bertani) plating medium (tryptone 10 g, yeast extract 5 g, NaCl 10 g, and agar 1.5%/L) containing chloramphenicol as the selective marker and incubated at 37° C. overnight to select microorganism strains displaying a resistance against chloramphenicol.

Strains selected as the template were directly subjected to PCR using primers of SEQ ID NO: 7 and 12 under the same conditions, and then the deletion of nadC gene was confirmed by identifying the gene size in wild strain and nadC-deficient strain to be 1.0 kb and 1.8 kb, respectively, on 1.0% agarose gel. In addition, nadC gene was also removed from *E. coli* W3110 as the wild strain according to the same method as above.

1-4. Preparation of Quinolinic Acid-Producing Strain

The pPro-nadBA plasmid constructed in Example 1-3 was used through CaCl$_2$ method to transform TF4076ΔnadC strain and W3110ΔnadC, as constructed in Example 1-3, which were then smeared on LB-Km plating medium (yeast extract 10 g/L, NaCl 5 g/L, tryptone 10 g/L, kanamycin 25 μg/L) and incubated at 37° C. overnight. Then, kanamycin-resistant 10 colonies were selected. The prepared strain for producing quinolinic acid thus constructed was designated as CV01-0009.

EXAMPLE 2

Preparation of Nicotinic Acid

2-1. Production of Quinolinic Acid

The strain producing quinolinic acid as prepared in Example 1 was incubated in LB-Km plating medium within the incubator at 37° C. overnight to obtain a single colony, which was then inoculated on 25 ml of quinolinic acid titer medium by 1 platinum loop and incubated with 250 rpm at 37° C. for 24 to 72 hours. The following Table 1 shows the composition of the medium for producing quinolinic acid.

TABLE 1

| Composition | Conc. (per L) |
|---|---|
| Glucose | 70 g |
| Ammonium Sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |

Quinolinic acid in the culture solution was analyzed by HPLC. The result of analysis is shown in the following Table 2, and indicates the ability of the strain to produce quinolinic acid.

TABLE 2

| Strains | Plasmids | Quinolinic acid (g/L) |
|---|---|---|
| W3110 | — | Not Detected (ND) |
|  | pPro-nadBA | ND |
| W3110ΔnadC | — | ND |
|  | pPro-nadBA | 0.4 |
| TF4076 | — | ND |
|  | pPro-nadBA | ND |
| TF4076ΔnadC | — | 0.1 |
|  | pPro-nadBA | 5.5 |

As shown in Table 2, when the expression of genes coding for aspartate oxidase and quinolinate synthetase was enhanced through promoter substitution in TF4076 derived from threonine-producing strain and W3110 strain as wild *E. coli*, quinolinic acid was not produced in both strains. The reason thereof is that all quinolinic acid produced is consumed in the NAD synthesis pathway due to the activity of quinolinate phosphoribosyltransferase.

On the contrary, the W3110ΔnadC strain, which was produced by removing quinolinate phosphoribosyltransferase to inhibit the decomposition of quinolinic acid produced in cells with quinolinate phosphoribosyltransferase and enhancing the expression of aspartate oxidase and quinolinate synthetase, produced quinolinic acid in an amount of 0.4 g/L. And the TF4076ΔnadC derived from threonine-producing strain, which was produced by removing quinolinate phosphoribosyltransferase to inhibit the decomposition of quinolinic acid produced in cells with quinolinate phosphoribosyltransferase and enhancing the expression of aspartate oxidase and quinolinate synthetase, produced quinolinic acid in an amount of 5.5 g/L, which is 13-times higher than the wild strain W3110ΔnadC, due to the biosynthetic pathway enhanced for aspartic acid, which is inherent in the strain itself. That is, it was confirmed that the strain modified by the combination of enhancement of the expression of aspartate oxidase and quinolinate synthetase, removal of the activity of quinolinate phosphoribosyltransferase, and enhancement of the biosynthetic pathway for producing aspartic acid can produce quinolinic acid at a higher efficiency than the existing strains.

2-2. Production of Nicotinic Acid Through Decarboxylation

Figure 3:
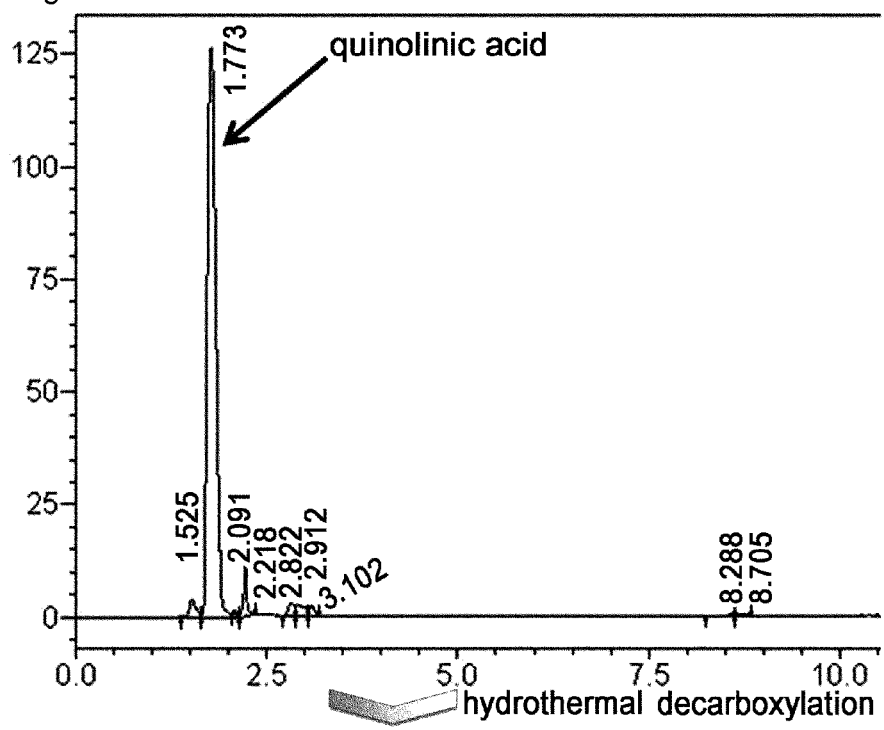
FIG. 3 shows the result of HPLC to identify quinolinic acid in the culture solution and nicotinic acid obtained after decarboxylation reaction of said culture solution, according to one embodiment of the present invention.
Figure 3:
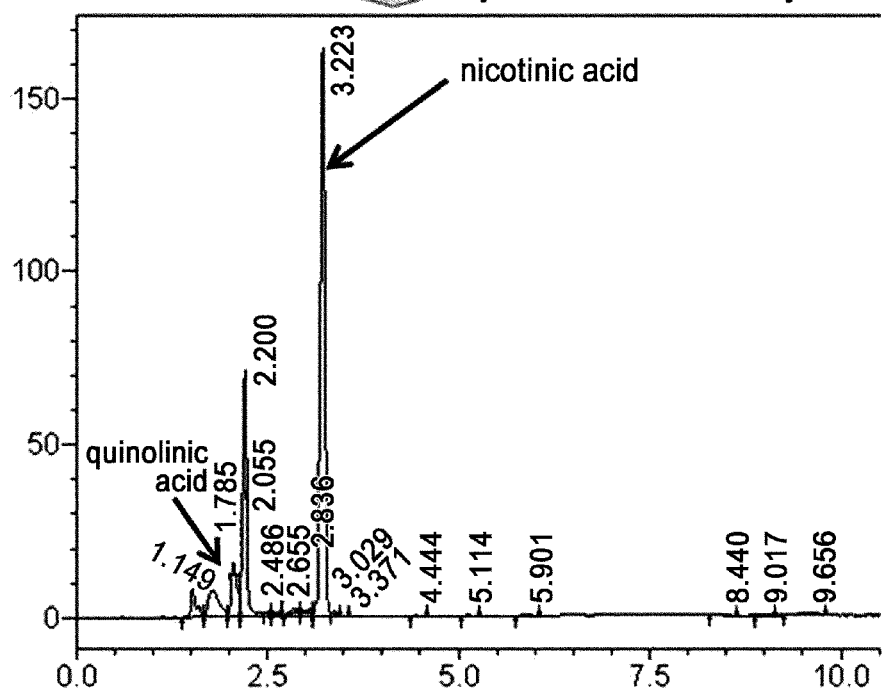

Decarboxylation reaction was conducted to convert quinolinic acid in the culture solution of quinolinic acid-producing strain, CV02-0009, which contains 5.5 g/L of quinolinic acid into nicotinic acid under high temperature and high pressure conditions. First, the culture solution containing quinolinic acid was centrifuged at 3000 to 4000 rpm for 10 to 30 minutes to remove cells in the culture solution. The supernatant containing quinolinic acid as obtained after centrifugation was used as the sample for decarboxylation reaction. The decarboxylation reaction was carried out under the conditions of 135° C. and 0.2 MPa for 3 hours, and the conditions of the sample as used are as shown in the following Table 3. Quinolinic acid comprised in deionized water as the experiment for the control group was the standard available from Sigma-Aldrich, and pH of aqueous quinolinic acid solution was titrated with sodium hydroxide, ammonia water, hydrochloric acid or sulfuric acid. The following Table 3 shows the rate of conversion of quinolinic acid into nicotinic acid by the reaction under high temperature and high pressure conditions. FIG. 3 shows the result of HPLC to identify quinolinic acid in the culture solution and nicotinic acid obtained after decarboxylation reaction of said culture solution.

TABLE 3

| Quinolinic Acid | Solution | pH (acid) | Nicotinic Acid | Yield g/g | Yield Molar basis |
|---|---|---|---|---|---|
| 5.5 g/L | deionized water | — | 3.8 g/L | 70% | 95% |
|  | Culture solution | 6-7 | ND | — | — |
|  |  | 2 (HCl) | 4.0 g/L | 73% | 99% |
|  |  | 3 (HCl) | 3.4 g/L | 63% | 85% |
|  |  | 2 ($H_2SO_4$) | 3.6 g/L | 66% | 90% |
|  |  | 3 ($H_2SO_4$) | 3.0 g/L | 55% | 75% |

The experiment to convert quinolinic acid into nicotinic acid using deionized water as the aqueous solution under the temperature and pressure conditions including 135° C. and 0.2 MPa, which are lower than 150 to 250° C. and 2 MPa conditions as disclosed in the prior reference Chinese Patent No. CN101353322C was conducted for 3 hours to obtain the result as shown in the above Table 3. This demonstrates that quinolinic acid was converted into nicotinic acid at up to 95% even under lower temperature and pressure conditions than those disclosed in said prior reference.

The experiment was conducted to convert quinolinic acid into nicotinic acid using the same method as that disclosed in the prior reference except that the fermentation culture solution was used as the aqueous solution of quinolinic acid. As a result, it could be identified that quinolinic acid was converted into nicotinic acid in deionized water, but not converted into nicotinic acid in the culture solution. The reason is that various ions present in the culture solution prevent the approach of hydrogen ion to the carboxyl group, and the movement of hydrogen ion as the requirements for decarboxylation of quinolinic acid. In order to solve this problem, it was intended to confirm whether the decarboxylation reaction occure or not in the fermentation culture solution containing quinolinic acid, through the method for increasing the chances to contact hydrogen ion with quinolinic acid in the fermentation culture solution by elevating the level of hydrogen ion. For this purpose, the pH value of the culture solution containing quinolinic acid was titrated from pH 6 to 7 to the range of pH 2 to 3 at which hydrogen ion can be maintained on high level. Said titration was conducted using hydrochloric acid or sulfuric acid.

As a result, the conversion rate of quinolinic acid into nicotinic acid was 85% to 99% when the ph value of the culture solution was titrated to pH 2 to 3 with the addition of hydrochloric acid, and 75% to 90% with the addition of sulfuric acid. According to this, nicotinic acid could be efficiently produced by addition of the acid and decarboxylation under mild temperature and pressure conditions as compared to the prior references, without additional purification of the culture solution obtained after the incubation of the microorganism strains.

The invention claimed is:

1. A method for the preparation of nicotinic acid, which comprises the steps of:
    obtaining a culture solution containing quinolinic acid by incubating a microorganism having an ability to produce quinolinic acid, in which the activity of quinolinate phosphoribosyltransferase is decreased relative to the wild-type or deleted and the activities of aspartate oxidase and quinolinate synthetase are increased relative to the wild-type; and
    adding an acid to the culture solution to decarboxylate quinolinic acid,
    wherein the microorganism having an ability to produce quinolinic acid belongs to *Enterbacter* genus, *Escherichia* genus, *Erwinia* genus, *Serratia* genus, *Providencia* genus, *Corynebacterium* genus or *Brevibacterium* genus.

2. The method according to claim 1, wherein the activity of quinolinate phosphoribosyltransferase of the microorganism is decreased relative to the wild-type or deleted by substituting a gene encoding the quinolinate phosphoribosyltransferase with a gene mutated to decrease the activity of quinolinate phosphoribosyltransferase, replacing an endogenous promoter for the gene with a promoter having weakened activity, or deleting the gene from chromosome.

3. The method according to claim 1, wherein the activities of aspartate oxidase and/or quinolinate synthetase of the microorganism are increased relative to the wild-type by increasing the intracellular copy number of genes encoding the aspartate oxidase and/or quinolinate synthetase, modifying expression regulatory sequences of the genes, or substituting the genes encoding the aspartate oxidase and/or quinolinate synthetase with genes mutated to increase the activities of aspartate oxidase and/or quinolinate synthetase.

4. The method according to claim 1, wherein the microorganism is a strain belonging to *Escherichia* genus.

5. The method according to claim 1, wherein the microorganism is *Escherichia coli*.

6. The method according to claim 1, wherein the microorganism is *Escherichia coli* deposited under accession number KCCM11165P.

7. The method according to claim 1, wherein the acid added to the culture solution is hydrochloric acid or sulfuric acid.

8. The method according to claim 1, wherein after addition of an acid, the culture solution has a pH value of 5 or less.

9. The method according to claim 1, wherein the decarboxylation reaction is conducted at a temperature ranges from 100° C. to 150° C.

10. The method according to claim 9, wherein the decarboxylation reaction is conducted at a temperature of 135° C.

11. The method according to claim 1, the decarboxylation reaction is conducted at a pressure ranges 0.1 MPa to 0.5 MPa.

12. The method according to claim 11, the decarboxylation reaction is conducted at a pressure of 0.2 MPa.

13. The method according to claim 1, further comprising the step of recovering and purifying nicotinic acid.

* * * * *

UNITED STATES PATENT AND TRADEMARK OFFICE
CERTIFICATE OF CORRECTION

| | | |
|---|---|---|
| PATENT NO. | : 9,297,030 B2 | Page 1 of 1 |
| APPLICATION NO. | : 13/979673 | |
| DATED | : March 29, 2016 | |
| INVENTOR(S) | : So Young Kim et al. | |

It is certified that error appears in the above-identified patent and that said Letters Patent is hereby corrected as shown below:

In the claims,

Column 34, Line 52, Claim 9:

After "conducted at a temperature"
Delete "ranges" and
Insert -- range --.

Column 34, Line 57, Claim 11:

After "conducted at a pressure"
Delete "ranges" and
Insert -- range --.

Signed and Sealed this
Twenty-eighth Day of June, 2016

Michelle K. Lee
*Director of the United States Patent and Trademark Office*